United States Patent
Greybush

(10) Patent No.: US 6,257,049 B1
(45) Date of Patent: Jul. 10, 2001

(54) AMBIENT HUMIDITY MEASUREMENT USING MICROWAVES

(75) Inventor: James J. Greybush, Allentown, PA (US)

(73) Assignee: Lucent Technologies, Inc., Murray Hill, NJ (US)

( * ) Notice: Subject to any disclaimer, the term of this patent is extended or adjusted under 35 U.S.C. 154(b) by 0 days.

(21) Appl. No.: 09/386,307

(22) Filed: Aug. 31, 1999

(51) Int. Cl.$^7$ .......................... G01R 27/04; G01W 1/00; G01N 33/00
(52) U.S. Cl. .................... 73/29.01; 73/31.01; 324/76.14; 324/640
(58) Field of Search ................................ 73/29.01, 29.03, 73/30.02, 31.01, 23.2, 30.1; 324/639, 640, 76.14, 76.56

(56) References Cited

U.S. PATENT DOCUMENTS

| | | | |
|---|---|---|---|
| 2,792,548 | * 5/1957 | Hershberger | 324/58.5 |
| 3,815,019 | * 6/1974 | Wiles | 324/58.5 A |
| 3,946,308 | * 3/1976 | Miura et al. | 324/58.5 C |
| 4,103,224 | * 7/1978 | Miura et al. | 324/58.5 C |
| 4,154,089 | * 5/1979 | Carlon | 73/29 |
| 4,576,036 | * 3/1986 | Huang et al. | 73/29 |
| 4,600,879 | * 7/1986 | Scully et al. | 324/58.5 A |
| 4,928,513 | * 5/1990 | Sugihara et al. | 73/1 G |
| 5,065,615 | * 11/1991 | Hill | 73/29.01 |
| 5,546,007 | * 8/1996 | Marvelli | 324/610 |
| 5,864,240 | * 1/1999 | Hirai et al. | 324/639 |
| 5,999,121 | * 12/1999 | Salonen | 342/351 |
| 6,035,698 | * 3/2000 | Lewin | 73/29.01 |

\* cited by examiner

*Primary Examiner*—Hezron Williams
*Assistant Examiner*—David J. Wiggins
(74) *Attorney, Agent, or Firm*—William H. Bollman

(57) ABSTRACT

A humidity sensor which utilizes microwave energy to determine a particular humidity value, e.g., a relative humidity, a specific humidity, or a dew point, without the need for delicate moving parts. The microwave humidity sensor requires little if any maintenance over a significantly long operational life, and is capable of highly accurate humidity measurements even at the extremes (e.g., toward 0% relative humidity and toward 100% relative humidity). In the disclosed embodiment, a microwave generator/transmitter is continuously or periodically pulsed to cause a known amount of microwave energy to be propelled through a metal tube structure, e.g., a waveguide tube structure. A microwave detector measures the amount of microwave energy at the other end of the tube structure. A processor measures the temperature of the ambient air within or just outside the tube structure and the pressure, and by measuring the output of the detector determines the amount of microwave energy which was absorbed during the passage through the tube structure. Given the amount of microwave energy absorbed and the temperature and pressure of the ambient air, a value for a desired humidity value is determined using interpolation as necessary from a look-up table containing empirically obtained absorption and temperature/pressure values for given humidity values.

23 Claims, 1 Drawing Sheet

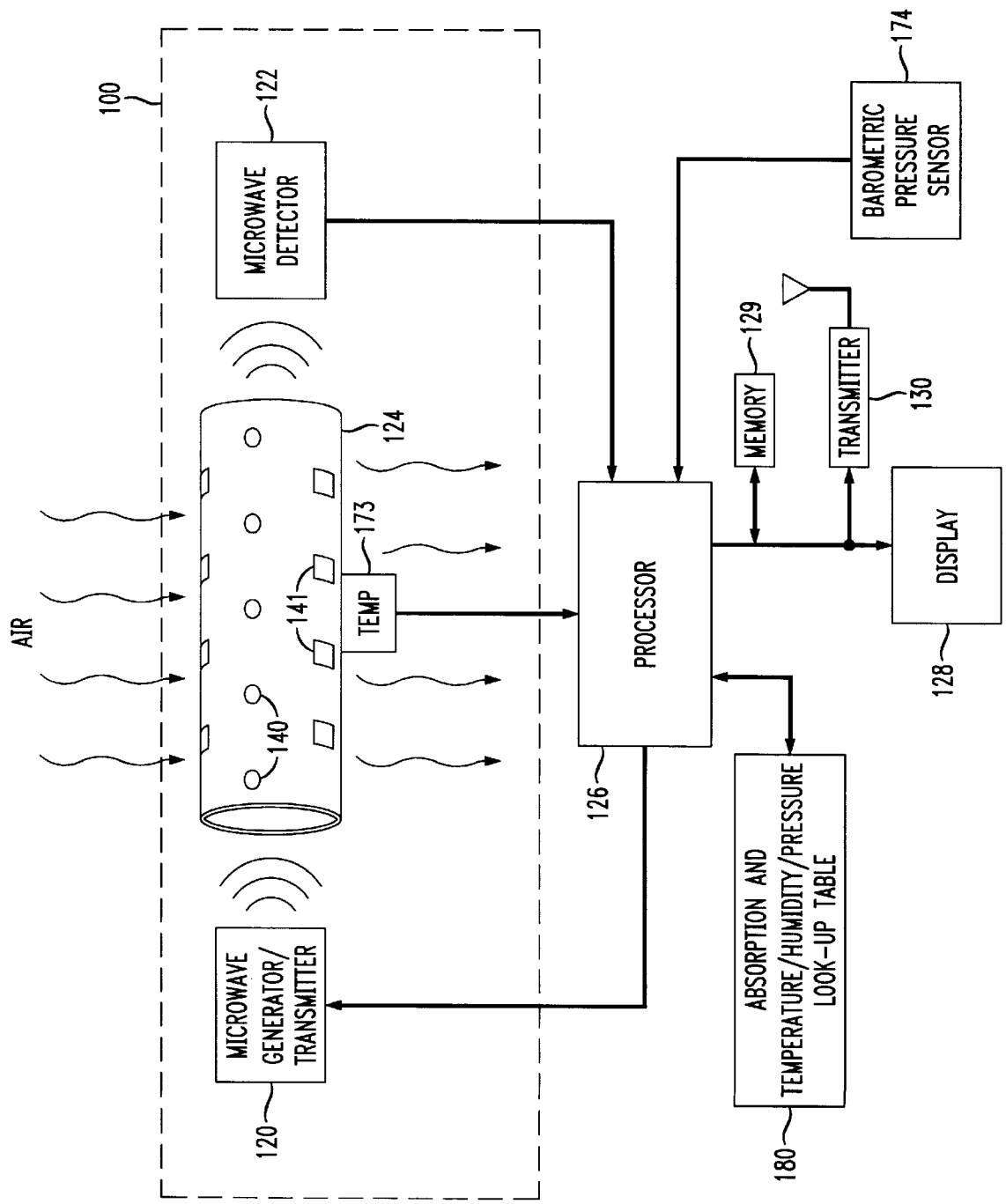

AMBIENT HUMIDITY MEASUREMENT USING MICROWAVES

BACKGROUND OF THE INVENTION

1. Field of the Invention

This invention relates generally to humidity sensors. More particularly, it relates to an apparatus and technique providing a more accurate, reliable and cost effective humidity sensor than is conventionally available.

2. Background of Related Art

Long term ambient humidity measurement is difficult to achieve with any high degree of accuracy or reliability.

Previous humidity sensors typically use mechanisms including delicate moving parts and materials having variable properties. One example of such a humidity sensor includes the use of a bundle of hair (e.g., blond human hair). Another is a coil enveloped in hydroscopic paper which expands/contracts with humidity. Such humidity sensors typically exhibit low measurement accuracy, particularly at the extremes of 0–20% and 80–100% humidity.

Humidity sensors having higher accuracy exist, but typically at the cost of higher maintenance and short accuracy lifetimes in the field. For instance, a humidity sensor using a chilled mirror is known wherein the mirror is chilled to the dew point which, along with the temperature, provides a fairly accurate humidity measurement. However, such higher accuracy humidity sensors, including lithium chloride and wet/dry bulb automated, are typically expensive to manufacture and require rigid and frequent maintenance (e.g., to clean the mirror).

Perhaps the more popular type of humidity sensor are solid state humidity sensors. While solid state humidity sensors are reasonably priced and accurate, they have been known to fail or degrade fairly quickly (e.g., after about 1 year or so), and thus tend to be both inaccurate and somewhat unreliable after a period of time.

Accordingly, there is a need for a humidity sensor which is accurate not only at a nominal humidity level but also at the extreme measurement levels, which is reliable, and which requires minimal if any maintenance.

SUMMARY OF THE INVENTION

In accordance with the principles of the present invention, a humidity sensor comprises a microwave transmitter and a microwave detector. A passage structure is between the microwave transmitter and the microwave detector. The passage structure includes at least one hole to allow ambient air to flow thereacross. A humidity value is calculated based on an absorption of microwave energy output by the microwave transmitter as measured by the detector.

A method of determining the humidity of ambient air in accordance with another aspect of the present invention comprises transmitting a known amount of microwave energy across the ambient air. An amount of absorption of microwave energy by water vapor contained in the ambient air is detected, and the amount of absorbed microwave energy is correlated to a particular value of humidity.

BRIEF DESCRIPTION OF THE DRAWINGS

Features and advantages of the present invention will become apparent to those skilled in the art from the following description with reference to the drawings, in which:

FIG. 1 shows a block diagram of an exemplary microwave humidity sensor constructed in accordance with the principles of the present invention.

DETAILED DESCRIPTION OF ILLUSTRATIVE EMBODIMENTS

The present invention provides the ability to accurately measure ambient humidity at a reasonable cost without the need for delicate moving parts, requiring minimal if any maintenance, and without the need for components which would degrade significantly over time.

In accordance with the principles of the present invention, the absorbency of microwave transmissions through a shielded structure such as a metal tube is measured and related directly to the humidity in ambient air passed through the tube.

FIG. 1 shows a block diagram of an exemplary microwave humidity sensor constructed in accordance with the principles of the present invention.

In particular, in FIG. 1, the basis of a microwave humidity sensor 100 is formed by a microwave generator/transmitter 120 fixed to one end of a metal structure 124 capable of containing an amount of microwave energy traversing an internal length thereof. The metal structure 124 includes a number of holes 140, 141 allowing passage of ambient air therethrough. The particular shapes of the holes 140, 141 is unimportant. To emphasize this, FIG. 1 depicts the use of two hole shapes, i.e., round holes 140 and square holes 141.

A microwave detector 122 is fixed to the other end of the transversed length of the metal structure (e.g., metal tube structure) 124. A temperature sensor 173 is preferably placed within or just outside the metal tube structure 124 to measure the temperature of ambient air within or just outside the metal tube structure 124. Additionally, a common solid state barometric pressure sensor 174 may be added to further increase the accuracy of the instrument at different barometric pressures, including those encountered at different altitudes. In addition to aiding in the calculation of humidity, the temperature and barometric pressure sensors output information can be displayed independently as part of a complete weather station.

A processor 126 is in communication with the microwave transmitter 120 to control the output of microwave energy from the microwave transmitter 120. The processor 126 is also in communication with the microwave detector 122, the temperature sensor 173, and the barometric pressure sensor 174.

The processor is also in communication with suitable calibration information, e.g., with an absorption & temperature/humidity/pressure value look-up table 180. The processor determines a desired humidity value, and provides the humidity value to a desired application device, e.g., to a display 128, to a memory location 129, and/or to a transmission device 130.

The microwave transmitter 120 is controlled by the processor 126 to output microwaves either continuously or in pulses. The output microwaves have a known amplitude and frequency. The amplitude and/or frequency of the microwaves are chosen such that the microwave energy is highly absorbed by water vapor in the ambient air passed through the tube structure 124. Generally speaking, the higher the absorption rate of the microwave energy into water vapor, the more accurate the microwave humidity sensor 100 will be.

The microwave frequency can be, e.g., similar to that used in conventional microwave ovens, The metal tube structure 124 need not be of any particular shape. A waveguide structure is shown in the exemplary embodiment, but square, circular, or other general shaped structures are equally applicable in accordance with the principles of the present invention.

In accordance with the principles of the present invention, the metal tube structure 124 includes a sufficient number of holes 140, 141 to allow for a free flow of ambient air into the metal tube structure 124. The holes 140, 141 are of sufficient size to allow the free flow of ambient air, yet are small enough to contain the microwave energy within the metal tube structure 124.

Depending upon the size and number of holes 140, 141 in the metal tube structure 124, some microwave energy transmitted by the microwave transmitter 120 may be allowed to leak outside the metal tube structure 124 without affecting significantly the capability of the microwave humidity sensor 100 in accordance with the principles of the present invention to measure humidity. This is because the amount of transmitted microwave energy leaking outside of the metal tube structure 124 will be constant, and will be accommodated for during a calibration process for the microwave humidity sensor 100.

The metal tube structure 124 can be of any suitable shape with the requirement that the pathway for the microwave energy through the ambient air be of sufficient length to provide the desired range, sensitivity, and accuracy for the microwave humidity sensor. Thus, the metal tube structure 124 can be, e.g., a straight structure as shown in FIGS. 1 and 2. Alternatively, the microwave energy can be directed about a curved structure (e.g., in the shape of a spiral) to allow a longer linear passage of the microwave energy output from the microwave transmitter 120 through a sampling of the ambient air before impinging upon the microwave detector 122.

The microwave detector 122 detects an amount of microwave energy impinging thereon, i.e., which was not absorbed by the water vapor in the ambient air passing through the metal tube structure 124.

The temperature of the ambient air is measured by a suitable temperature sensor appropriately located to measure the temperature of the ambient air (e.g., midway through the metal tube structure 124). Suitable temperature sensors include a thermistor or a semiconductor temperature sensor.

The amplitude of the energy detected by the microwave detector 122 is compared to the amplitude of the microwave energy transmitted by the microwave transmitter 120. Given this comparison and the temperature of the ambient air and pressure, a desired value corresponding to humidity can be determined, e.g., by a suitable processor.

In particular, in accordance with the principles of the present invention, the amount of loss of the transmitted microwave energy after passing through the metal tube structure 124 is proportional to the amount of water vapor in the ambient air inside the metal tube structure 124.

The processor 126 may be any suitable processor, e.g., a microcontroller, a microprocessor, or a digital signal processor (DSP). The processor may or may not be dedicated for use by the microwave humidity sensor 100.

The processor 126 retrieves the calibration factor for the microwave humidity sensor 100, and performs calculations necessary to determine the amount of loss of the microwave energy caused by the absorption by water vapor in the ambient air. Given the amount of absorption of microwave energy, and the temperature of the ambient air and pressure, an accurate value for a desired humidity value (e.g., relative humidity, specific humidity, dew point, etc.) can be determined from an appropriate look-up table 180 associating such measurements to known values for the desired humidity value.

The contents of the absorption & temperature/humidity/pressure look-up table 180 can be determined empirically during a calibration process. Thus, for given values of humidity, temperature and pressure, exact absorption values can be measured and stored in an appropriate memory area accessible by the processor 126.

Any particular humidity value may be determined by the processor 126. For instance, given the measured absorption loss of the microwave energy and the temperature and pressure of the ambient air, a relative humidity, specific humidity, and/or dew point can be calculated.

Preferably, the microwave humidity sensor 100 is calibrated before use to determine the amount of microwave energy transmitted by the microwave transmitter 120 which would be detected by the microwave detector 122 if none of the energy is absorbed by water vapor in the intervening ambient air. To this end, the microwave humidity sensor 100 may be calibrated in a suitable 0% humidity environment, e.g., in a vacuum, or in air with all water vapor removed.

The calibration information is stored in an appropriate register location within the processor 126 or other memory location. For instance, the calibration information can be stored in the form of a look-up table as shown in FIG. 1.

The specific calibration information contained in the absorption & temperature/humidity/pressure value look-up table 180 can be determined on a device-by-device basis for the highest accuracy, or can be determined for a specific model of the microwave humidity sensor 100 and pre-stored in a manufacturing process, but this may result in lower accuracy.

Accuracy of the humidity value measured by the microwave humidity sensor 100 can be improved by the use of finer increments in the calibration information contained in the absorption & temperature/humidity/pressure value look-up table 180.

Accuracy can also be improved by interpolating between the discrete calibration information and humidity values contained in the absorption & temperature/humidity/pressure value look-up table 180 when comparing the discrete values with particularly measured values for absorption, temperature and pressure during the operation of the microwave humidity sensor 100.

The resultant humidity value determined by the processor 126 may be output to a suitable device relevant to the particular application. For instance, the humidity value may be converted to a relative humidity measurement, a dew point measurement, and/or a specific humidity measurement, and displayed on a suitable display, or logged in an appropriate log file or transmitted to another location.

The present invention provides a humidity sensor which utilizes microwave energy to determine a particular humidity value, e.g., a relative humidity, a specific humidity, or a dew point, without the need for delicate moving parts. The microwave humidity sensor requires little if any maintenance over a significantly long operational life, and is capable of highly accurate humidity measurements even at the extremes (e.g., toward 0% relative humidity and toward 100% relative humidity).

While the invention has been described with reference to the exemplary embodiments thereof, those skilled in the art will be able to make various modifications to the described embodiments of the invention without departing from the true spirit and scope of the invention.

What is claimed is:

1. A humidity sensor comprising:

a microwave transmitter;

a microwave detector;

a calibrator utilizing at least one of temperature sensor and barometric pressure to determine a calibration value in a calibration look-up table; and a passage structure between said microwave transmitter and said microwave detector, said passage structure including at least one hole to allow ambient air to flow thereacross;

wherein a humidity value is calculated based on an absorption of microwave energy output by said microwave transmitter as measured by said detector and said calibration value.

2. The humidity sensor according to claim 1, wherein:

said passage structure includes a plurality of holes to allow said ambient air to flow thereacross.

3. The humidity sensor according to claim 1, wherein:

said passage structure is formed of a waveguide.

4. The humidity sensor according to claim 1, wherein:

said passage structure is metallic.

5. The humidity sensor according to claim 1, wherein:

said at least one hole in said passage structure allows said ambient air to flow therethrough but contains therein a significant amount of microwave energy output by said microwave transmitter.

6. The humidity sensor according to claim 1, wherein said humidity value is one of:

relative humidity;

specific humidity; and dew point.

7. The humidity sensor according to claim 1, further comprising:

a plurality of calibration values correlating absorption of microwave energy to corresponding humidity values.

8. The humidity sensor according to claim 7, wherein:

said plurality of calibration values correlate temperature and pressure in addition to said absorption of microwave energy to corresponding humidity values.

9. The humidity sensor according to claim 1, further comprising:

a processor in communication with said microwave detector.

10. The humidity sensor according to claim 7, further comprising:

a processor in communication with said microwave detector.

11. The humidity sensor according to claim 1, wherein:

said calibration look-up table contains empirically determined values.

12. A method of determining a humidity of ambient air, comprising:

transmitting a known amount of microwave energy across said ambient air;

detecting an amount of absorption of microwave energy by water vapor contained in said ambient air;

determining a calibration value based on at least one of temperature and barometric pressure from a calibration look-up table; and correlating said amount of absorbed microwave energy to a particular value of humidity based on said calibration value.

13. The method of determining a humidity of ambient air according to claim 12, wherein said value of humidity is one of:

relative humidity;

specific humidity; and dew point.

14. The method of determining a humidity of ambient air according to claim 12, further comprising:

measuring a temperature and pressure of said ambient air.

15. The method of determining a humidity of ambient air according to claim 14, wherein:

said step of correlating said amount of absorbed microwave energy to said particular value of humidity includes correlation of said measured temperature and pressure to said absorbed microwave energy.

16. The method of determining a humidity of ambient air according to claim 12, further comprising:

passing said ambient air through a microwave pipe waveguide.

17. The method of determining a humidity of ambient air according to claim 11, wherein said value of humidity is one of:

said calibration look-up table contains empirically determined values.

18. Apparatus for determining a humidity of ambient air, comprising:

means for transmitting a known amount of microwave energy across said ambient air;

means for detecting an amount of absorption of microwave energy by water vapor contained in said ambient air; and means for determining a calibration value based on at least one of temperature and barometric pressure from a calibration look-up table; and means for correlating said amount of absorbed microwave energy to a particular value of humidity based on said calibration value.

19. The apparatus for determining a humidity of ambient air according to claim 18, wherein said value of humidity is one of:

relative humidity;

specific humidity; and dew point.

20. The apparatus for determining a humidity of ambient air according to claim 18, further comprising:

means for measuring a temperature and pressure of said ambient air.

21. The apparatus for determining a humidity of ambient air according to claim 20, wherein:

said means for correlating said amount of absorbed microwave energy to said particular value of humidity further correlates said measured temperature and pressure to said absorbed microwave energy.

22. The apparatus for determining a humidity of ambient air according to claim 18, further comprising:

means for passing said ambient air through a microwave pipe waveguide.

23. The apparatus for determining a humidity of ambient air according to claim 18, wherein said value of humidity is one of:

said calibration look-up table contains empirically determined values.

* * * * *